United States Patent [19]
Yeung et al.

[11] Patent Number: 5,498,324
[45] Date of Patent: Mar. 12, 1996

[54] MULTIPLEXED FLUORESCENCE DETECTOR SYSTEM FOR CAPILLARY ELECTROPHORESIS

[75] Inventors: Edward S. Yeung, Ames; John A. Taylor, Nevada, both of Iowa

[73] Assignee: Iowa State University Research Foundation, Inc., Ames, Iowa

[21] Appl. No.: 223,864

[22] Filed: Apr. 6, 1994

Related U.S. Application Data

[63] Continuation of Ser. No. 13,960, Feb. 5, 1993, Pat. No. 5,324,401.

[51] Int. Cl.$^6$ .................. G01N 27/26; G01N 27/447
[52] U.S. Cl. .................. 204/452; 204/603; 356/344
[58] Field of Search .................. 204/180.1, 299 R; 356/344

[56] References Cited

U.S. PATENT DOCUMENTS

| | | | |
|---|---|---|---|
| 4,675,300 | 6/1987 | Zare et al. | 204/180.1 X |
| 4,729,947 | 3/1988 | Middendorf et al. | 204/182.8 X |
| 4,891,120 | 1/1990 | Sethi et al. | 204/299 R |
| 4,927,265 | 5/1990 | Brownlee | 204/180.1 |
| 5,006,210 | 4/1991 | Yeung et al. | 204/180.1 |
| 5,021,646 | 6/1991 | Weinberger et al. | 204/180.1 |
| 5,114,551 | 5/1992 | Hjerten et al. | 204/180.1 |
| 5,274,240 | 12/1993 | Mathies et al. | 250/458.1 |
| 5,324,401 | 6/1994 | Yeung et al. | 204/180.1 |

OTHER PUBLICATIONS

Y. Baba et al., "Gel-filled capillaries for nucleic acid separations in capillary electrophoresis", *Trends in Anal. Chem.*, 11, 280–287 (1992).

G. M. Church et al., "Multiplex DNA Sequencing", *Science*, 240, 185–188 (Apr. 1988).

A. S. Cohen et al., "Rapid separation and purification of oligonucleotides by high-performance capillary gel electrophoresis", *Proc. Natl. Acad. Sci., U.S.A.*, 85, 9660–9663 (Dec. 1988).

P. M. Epperson et al., "Applications of Charge Transfer Devices in Spectroscopy", *Anal. Chem.*, 60, 327A–335A (Mar. 1988).

X. C. Huang et al., "Capillary Array Electrophoresis Using Laser-Excited Confocal Fluorescence Detection", *Anal. Chem.*, 64, 967–972 (Apr. 1992).

X. C. Huang et al., "DNA Sequencing Using Capillary Array Electrophoresis", *Anal. Chem.*, 64, 2149–2154 (Sep. 1992).

L. B. Koutny et al., "Expert System for Data Acquisition to Achieve a Constant Signal–to–Noise Ratio: Application to Imaging for DNA Sequencing Gels", *Anal. Chem.*, 65, 148–152 (Jan. 1993).

T. T. Lee et al., "Facilitating Data Transfer and Improving Precision in Capillary Zone Electrophoresis with Migration Indices", *Anal. Chem.*, 63, 2842–2848 (Dec. 1991).

T. T. Lee et al., "Compensating for Instrumental and Sampling Biases Accompanying Electrokinetic Injection in Capillary Zone Electrophoresis", *Anal. Chem*, 64, 1226–1231 (Jun. 1992).

R. E. Milofsky et al., "Native Fluorescence Detection of Nucleic Acids and DNA Restriction Fragments in Capillary Electrophoresis", *Anal. Chem.*, 65, 153–157 (Jan. 1993).

M. A. Quesada et al., "High–Sensitivity DNA Detection with a Laser-Excited Confocal Fluorescence Gel Scanner", *BioTechniques*, 19(10), 616–625 (1991).

J. V. Sweedler et al., "High–Performance Charge Transfer Device Detectors", *Anal. Chem.*, 60, 282A–291A (Feb. 1988).

(List continued on next page.)

*Primary Examiner*—John Niebling
*Assistant Examiner*—John S. Starsiak, Jr.
*Attorney, Agent, or Firm*—Schwegman, Lundberg & Woessner

[57] ABSTRACT

A fluorescence detection system for capillary electrophoresis is provided wherein the detection system can simultaneously excite fluorescence and substantially simultaneously monitor separations in multiple capillaries. This multiplexing approach involves laser irradiation of a sample in a plurality of capillaries through optical fibers that are coupled individually with the capillaries. The array is imaged orthogonally through a microscope onto a charge-coupled device camera for signal analysis.

15 Claims, 8 Drawing Sheets

OTHER PUBLICATIONS

J. V. Sweedler et al., "Fluorescence Detection in Capillary Zone Electrophoresis Using a Charge–Coupled Device with Time–Delayed Integration", *Anal. Chem.*, 63, 496–502 (Mar. 1991).

H. Swerdlow et al., "Three DNA Sequencing Methods Using Capillary Gel Electrophoresis and Laser–Induced Fluorescence", *Anal. Chem.*, 63, 2835–2841 (Dec. 1991).

S. Takahashi et al., "Installation of Multi–Capillary Electrophoresis", *Proceedings of Capillary Electrophoresis Symposium*, Dec., 1992 (English Abstract).

J. A. Taylor et al., "Axial–Beam Laser–Excited Fluorescence Detection in Capillary Electrophoresis", *Anal. Chem.*, 64, 1741–1744 (Aug. 1992).

G. L. Trainor, "DNA Sequencing, Automation, and the Human Genome", *Anal. Chem.*, 62, 418–426 (Mar. 1990).

C.–W. Whang et al., "Temperature Programming in Capillary Zone Electrophoresis", *Anal. Chem.*, 64, 502–506 (Mar. 1992).

E. S. Yeung et al., "Laser Fluorometric Detection in Liquid Chromatography", *Anal. Chem.*, 52, 1465A–1481A (1980).

E. S. Yeung, "Quantitation in Electrophoresis Based on Lasers", Abstract of Grant No. OHER–RPIS 4992 obtained from the Dialog On–Line database Federal Research in Progress.

E. S. Yeung, "Genome", Abstract of Gran No. WPAS–93/CH–AMES/00 obtained from the Dialog On–Line database Federal Research in Progress.

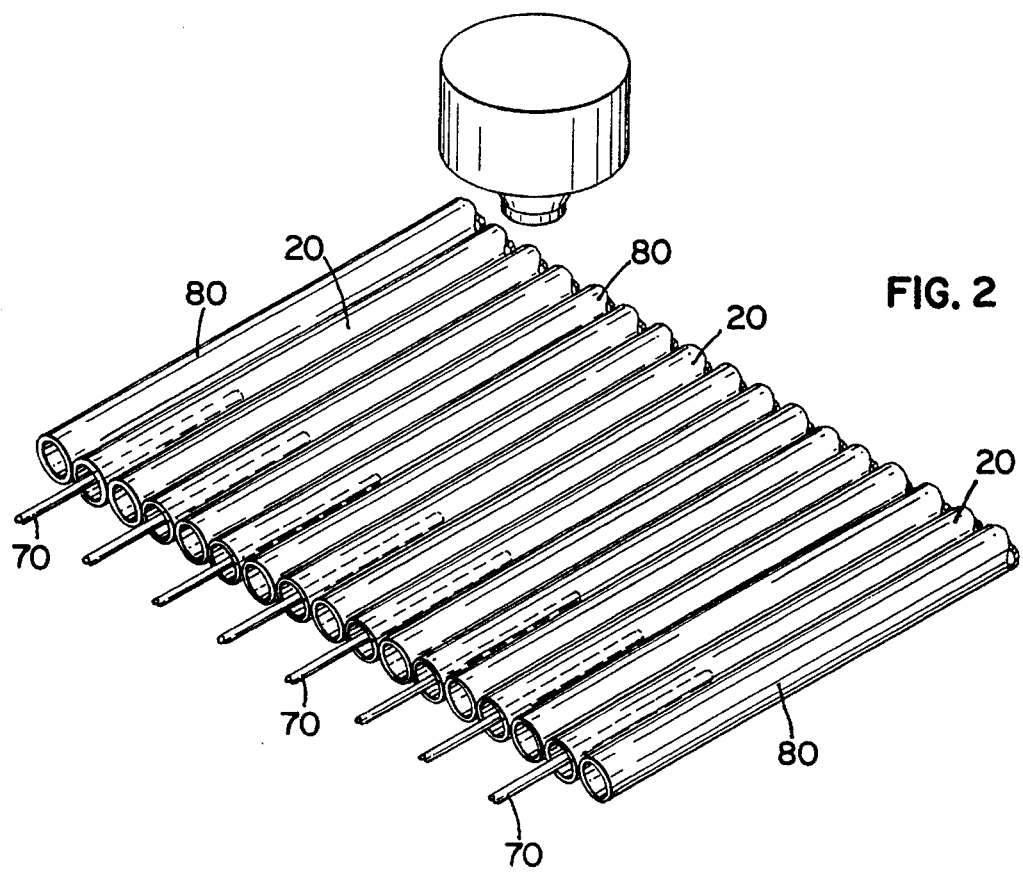
FIG. 2
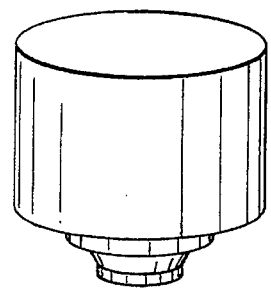
FIG. 3
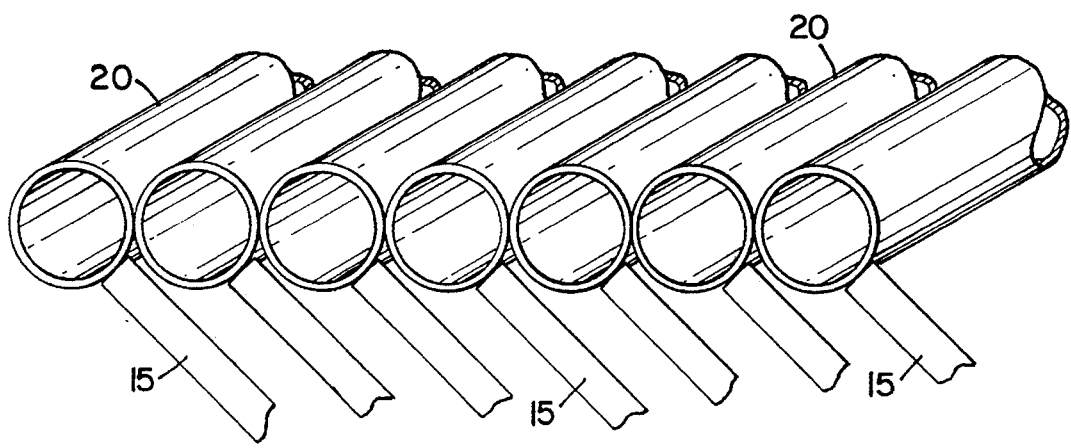

MULTIPLEXED FLUORESCENCE DETECTOR SYSTEM FOR CAPILLARY ELECTROPHORESIS

STATEMENT OF GOVERNMENT RIGHTS

The present invention was made with Government support under Grant No. W7405-ENG-82 awarded by the U.S. Department of Energy. The Government has certain rights in the invention.

This is a continuation of application Ser. No. 08/013,960, filed Feb. 5, 1993 now U.S. Pat. No. 5,324,401.

FIELD OF THE INVENTION

The present invention relates to fluorescence detector systems for capillary electrophoresis. Specifically, the present invention relates to fluorescence detector systems with the ability to substantially simultaneously excite fluorescence and to substantially simultaneously monitor separations in multiple capillaries.

BACKGROUND OF THE INVENTION

Electrophoresis is an electrochemical process in which molecules with a net charge migrate in a solution under the influence of an electric current. Traditionally, slab gel electrophoresis has been a widely used tool in the analysis of genetic materials. See, for example, G. L. Trainor, Anal. Chem., 62, 418–426 (1990). Recently, capillary electrophoresis (CE) has emerged as a powerful separations technique, with applicability toward a wide range of molecules from simple atomic ions to large DNA fragments. In particular, capillary gel electrophoresis (CGE) has become an attractive alternative to slab gel electrophoresis (SGE) for biomolecule analysis, including DNA sequencing. See, for example, Y. Baba et al., Trends in Anal. Chem., 11, 280–287 (1992). This is generally because the small size of the capillary greatly reduces Joule heating associated with the applied electrical potential. Furthermore, CGE produces faster and better resolution than slab gels. Because of the sub-nanoliter size of the samples involved, however, a challenging problem in applying this technology is the detecting and monitoring of the analytes after the separation.

Currently, sophisticated experiments in chemistry and biology, particularly molecular biology, involve evaluating large numbers of samples. For example, DNA sequencing of genes are time consuming and labor intensive. In the mapping of the human genome, a researcher must be able to process a large number of samples on a daily basis. If many capillaries of CE can be conducted and monitored simultaneously, i.e., multiplexed, cost and labor for such projects can be significantly reduced. Attempts have been made to sequence DNA in slab gels with multiple lanes to achieve multiplexing. However, slab gels are not readily amenable to a high degree of multiplexing and automation. Difficulties exist in preparing uniform gels over a large area, maintaining reproducibility over different gels, and loading sample wells. Furthermore, difficulties arise as a result of the large physical size of the medium, the requirement of uniform cooling, large amounts of media, buffer, and samples, and long run times for extended reading of nucleotides. Unless gel electrophoresis can be highly multiplexed and run in parallel, the advantages of capillary electrophoresis cannot produce substantial gain in shortening the time needed for sequencing the human genome.

Significantly, the capillary format is in fact well suited for multiplexing. The substantial reduction of Joule heating per lane makes the overall cooling and electrical requirement more manageable. The cost of materials per lane is reduced because of the smaller sample sizes. The reduced band dimensions are ideal for excitation by laser beams and for imaging onto solid-state array detectors. The use of electromigration injection, i.e., applying the sample to the capillary by an electrical field, provides reproducible sample introduction with little band spreading and with little labor.

Among the techniques used for detecting target species in capillary electrophoresis, laser-excited fluorescence detection so far has provided the lowest detection limits. Therefore, fluorescence detection has been used for the analysis of chemicals, especially macromolecules in capillary electrophoresis. For example, Zare et al. (U.S. Pat. No. 4,675,300) discussed a fluoroassay method for the detection of macromolecules such as genetic materials and proteins in capillary electrophoresis. Yeung et al. (U.S. Pat. No. 5,006,210) presented a system for capillary zone electrophoresis with laser-induced indirect fluorescence detection of macromolecules, including proteins, amino acids, and genetic materials.

Systems such as these generally involve only one capillary. There have been attempts to implement the analysis of more than one capillary simultaneously in the electrophoresis system, but the number of capillaries has been quite small. For example, S. Takahashi et al., Proceedings of Capillary Electrophoresis Symposium, December, 1992, referred to a multi-capillary electrophoresis system in which DNA fragment samples were analyzed by laser irradiation causing fluorescence. This method, however, relies on a relatively poor focus (large focal spot) to allow coupling to only a few capillaries. Thus, this method could not be applied to a large number of capillaries, such as 1000 capillaries, for example. This method also results in relatively low intensity and thus poor sensitivity because of the large beam. Furthermore, detection in one capillary can be influenced by light absorption in the adjacent capillaries, thus affecting accuracy.

Attempts have been made to perform parallel sequencing runs in a set of up to 24 capillaries by providing laser-excited fluorometric detection and coupling a confocal illumination geometry to a single laser beam and a single photomultiplier tube. See, for example, X. C. Huang et al., Anal. Chem., 64, 967–972 (1992), and Anal. Chem., 64, 2149–2154 (1992). However, observation is done one capillary at a time and the capillary bundle is translated across the excitation/detection region at 20 mm/sec by a mechanical stage.

There are features inherent in the confocal excitation scheme that limit its use for very large numbers (thousands) of capillaries. Because data acquisition is sequential and not truly parallel, the ultimate sequencing speed is generally determined by the observation time needed per DNA band for an adequate signal-to-noise ratio. Having more capillaries in the array or being able to translate the array across the detection region faster will not generally increase the overall sequencing speed. To achieve the same signal-to-noise ratio, if the state-of-the-art sequencing speed of 1000 nucleotides/hour/lane is used, the number of parallel capillaries will have to be reduced proportionately regardless of the scan speed. Moreover, the use of a translational stage can become problematic for a large capillary array. Because of the need for translational movement, the amount of cycling and therefore bending of the capillaries naturally increases with the number in the array. It has been shown that bending of the capillaries can result in loss in the separation efficiency.

This is attributed to distortions in the gel and multipath effects. Sensitive laser-excited fluorescence detection also requires careful alignment both in excitation and in light collection to provide for efficient coupling with the small inside diameter (i.d.) tubing and discrimination of stray light. The translational movement of the capillaries thus has to maintain stability to the order of the confocal parameter (around 25 μm) or else the cylindrical capillary walls will distort the spatially selected image due to misalignment of the capillaries in relation to the light source and photodetector.

Further, the standard geometry for excitation perpendicular to the axis of the capillary requires the creation of an optically clear region in the capillary. This makes the capillary fragile and complicates the preparation of capillaries for use. Moreover, the excitation path length, and hence the fluorescence signal, is restricted to the small diameter of the capillary. Therefore, there is a need for a fluorescence detection system that can be utilized to analyze a large number of samples substantially simultaneously without bulky equipment and unduly complicated procedures such as careful alignment.

SUMMARY OF THE INVENTION

The present invention provides a fluorescence detection system for capillary electrophoresis wherein a laser can be used to substantially simultaneously excite fluorescence in multiple capillaries and a detector can substantially simultaneously monitor analyte separations by detecting the fluorescence in a plurality of separation capillaries. This multiplexing approach involves laser illumination of a bundle of optical fibers that are coupled individually with the capillaries in a capillary array. The coupling can be done by inserting at least one optical fiber into each capillary that contains sample. It can also be accomplished by placing the optical fiber adjacent to and perpendicular in relation to the capillary. The fluorescence of the array of capillaries is focused orthogonally, i.e., perpendicularly in relation to the length of the capillaries, through a lens such as a microscope or camera lens and imaged onto a charge-coupled-device camera for signal analysis. The technique can be used for monitoring as many capillaries as desired, from at least 2 to more than 1000 capillaries.

The multiplexed fluorescence detection system contains an array of at least two (but possibly thousands) of capillaries, each preferably having an inside diameter of about 20–500 microns, and an array of at least two (but possibly thousands) of optical fibers of a suitable outside diameter. Each capillary has an annular wall, an intake end, and an exit end. A more preferable inside diameter of each capillary is about 40–100 microns. The multiplexed fluorescence detection system contains a laser for generating coherent light of a wavelength suitable for exciting fluorescence in a fluorescent species and a means for detecting the fluorescent light emitted by the fluorescent species through the wall of each capillary.

An argon laser is a preferred means for generating coherent light in the present invention, although any laser with the proper power and wavelength for excitation of the fluorescent species can be used. A beam from the laser is focused through a microscope objective onto the ends of the optical fibers distal to the capillaries. Light is therefore transmitted axially, i.e., parallel to the length of the capillaries, into the cores of the capillaries by means of the optical fibers. Alternatively, light is transmitted through the capillary wall of each of the capillaries with an optical fiber placed perpendicular in relation to each capillary. Each capillary has a detection zone where the fluorescence is transmitted through the capillary wall. The detection zones of the capillaries are imaged onto a charged-coupled device imaging system, or (CCD) camera, through a microscope. Data is extracted from the memory of the CCD camera and analyzed by a computer. Instead of a CCD system, a charge injection device based (CID) imaging system can also be used.

The present invention can be applied to a direct fluorescence system or an indirect fluorescence system. In a direct fluorescence system, the presence of a target fluorescent species is detected by a change, typically an increase in the fluorescence recorded by the detector as the target fluorescent species passes the detection zone. In an indirect fluorescence system, the buffer solution contains a background fluorophore. As the target analyte species traverses the detection zone, laser induced fluorescence results in either displacement or ion pairing of an ionic analyte with the fluorophore.

The present invention can be implemented utilizing an array of capillaries containing preferably at least about 100 capillaries, and more preferably at least about 500 capillaries, and most preferably at least about 1000 capillaries. It is necessary to select a material of construction for the capillaries such that at least part of each capillary is translucent to light of a wavelength of about 200–1,500 nm, so that fluorescent light can pass through the capillary wall. Inorganic materials such as quartz, glass, fused silica, and organic materials such as teflon and its related materials, polyfluoroethylene, aramide, nylon, polyvinyl chloride, polyvinyl fluoride, polystyrene, polyethylene and the like can be used.

Any conventional fluorescence labels such as a salicylate, dansyl chloride, ethidium bromide, rhodamine, fluorescein, fluorescein isothiocyanate, and the like can be used. To eliminate or reduce photochemical bleaching (i.e., a reduction in the fluorescent properties of fluorophores) of the fluorescent labels, an organic absorber, such as Orange G, which is a dye, can be used to reduce bleaching of the fluorophores before they reach the detection zone of the capillaries. In the case of a partial internal reflection system, a bend can be made in the capillary after the detection zone to prohibit any further light travel through the liquid core.

Spacers are preferably placed between each of the separation capillaries to reduce crosstalk, which is the interference between the separation capillaries due to the emission of fluorescence light in the adjacent capillaries. Fibers, capillaries, thin pieces of paper of dark color and the like can be used as spacers.

This multiplexed detection system can be used for analyzing macromolecules such as proteins, amino acids, polypeptides, carbohydrates, polysaccharides, oligo-nucleotides, nucleic acids, RNAs, DNAs, bacteria, viruses, chromosomes, genes, organelles, fragments, and combinations thereof. This invention is also equally applicable whether a gel is used in the capillary electrophoresis system or not.

A method for detecting macromolecules, such as biological molecules, using a multiplexing approach is also provided. According to this method, samples are introduced, optionally with fluorophores, into capillaries of a capillary array in a capillary electrophoresis system. Coherent light emitted by a laser is transmitted through optical fibers coupled to the capillaries. The change in fluorescence emitted by the fluorescent species is detected orthogonally by a CCD or CID camera through a microscope.

BRIEF DESCRIPTION OF THE DRAWINGS

FIG. 2 is a schematic representation of a portion of an interface between capillaries and optical fibers.

FIG. 3 is a schematic representation of an alternative multiplexed detection system in capillary electrophoresis wherein orthogonal irradiation is used.

DETAILED DESCRIPTION OF THE INVENTION

Figure 1:
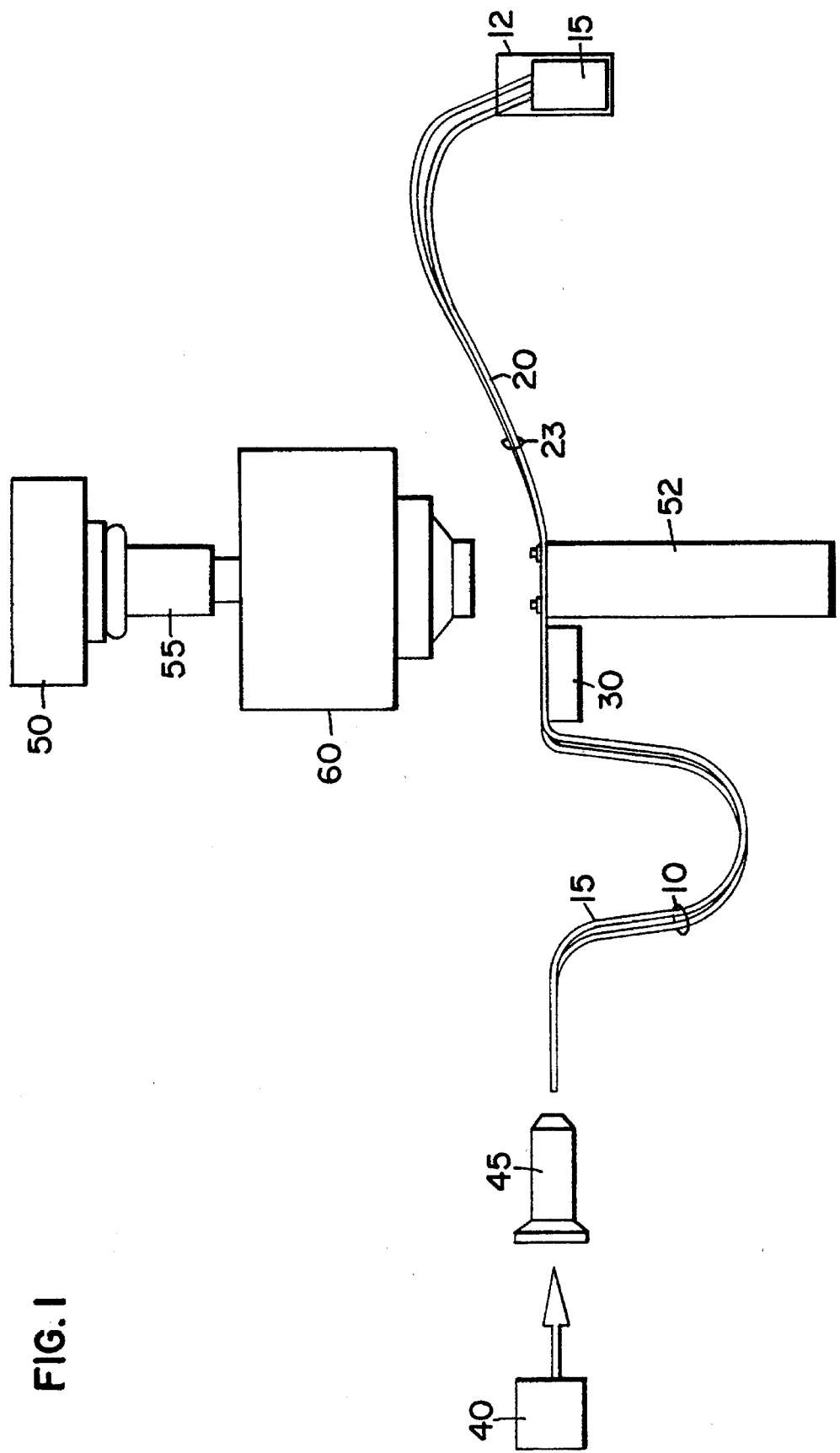
FIG. 1 is schematic representation of a preferred multiplexed detection system in capillary electrophoresis utilizing axial irradiation.

The present invention provides a fluorescence detector system, i.e., fluorescence detection system, for capillary electrophoresis wherein a laser can substantially simultaneously excite fluorescence in analyte in multiple capillaries and a detector can substantially simultaneously monitor separations of analytes, i.e., target species, in a plurality of capillaries. Herein, "a plurality" means at least two. In this system, an excitation laser is coupled to a plurality of optical fibers that are in turn individually coupled with the capillaries. The technique of the present invention can be used for monitoring as many capillaries as desired, even up to thousands of capillaries and more. Furthermore, data collection rates are much faster in this system than in conventional CGE. Significantly, the present invention allows for future increases in sequencing rates as permitted by advances in optics and capillary technology.

In capillary electrophoresis (CE), typically analytes, i.e., target species, are detected by measuring laser-induced fluorescence emitted by the target species. Fluorescence is a phenomenon in which an atom or molecule emits light when passing from a higher to a lower electronic state. A fluorescent species is excited by absorption of electromagnetic radiation of a proper wavelength. It emits light of a longer wavelength when it passes from the high energy state to a low energy state. The time interval between absorption and emission of energy is extremely short, typically within a range of about $10^{-8}$-$10^{-3}$ seconds. Some analyte molecules such as DNAs can be fluorescent naturally and gives off native fluoescences when irridated with a light of suitable wave length. Other molecules, such as proteins, may need to be tagged with fluorophores to become fluorescent. The present invention is a system for detection of such laser-excited fluorescence. This invention can also be used for the detection of phosphorescence in which the time interval between absorption and admission of energy is much longer. As used herein, the term "fluorescence" includes fluorescent phenomenon as well as phosphorescent phenomenon.

Fluorescence is measured by a detector at a detection zone of a capillary. During the process of electrophoresis, as a fluorescent species traverses the detection zone, it is excited by an incident laser beam. In a direct fluorescence detection system, either the target species is fluorescent, or it is transformed into a fluorescent species by linking with a fluorophore. The passing of the fluorescent species across the detection zone results in a change, typically an increase in the fluorescence that is detectable.

It is also possible to employ other schemes of fluorescence. For example, instead of producing an increase in fluorescence it is possible to have a change in the spectral characteristics of the fluorescent species. The change in the emitted fluorescence spectrum can be detected as a change in the intensity of light of particular wavelengths. Another applicable system is the use of indirect fluorometry. Such a system is described by Yeung et al. in U.S. Pat. No. 5,006,210. In this method, a fluorescent ion or fluorophore is added to a buffer solution as a principal component of the buffer. As these fluorophore components in the buffer pass the detection zone, laser induced fluorescence results in chemical reaction of the ionic analyte with the fluorophore. This produces a change in fluorescence, a signal which can be detected by a camera through a microscope.

The Detection System

FIG. 1 is a schematic representation of the application of the multiplexed detection system 100 in capillary electrophoresis. Container 12 contains a buffer solution 25 that is in fluid communication with each individual capillary 20 of an array 23 of capillaries 20 of the electrophoresis system 100. Each capillary 20 has a high voltage end 13 and a low voltage end 33 (see FIG. 2). The high voltage end 13 of each capillary 20 is immersed in buffer 25 and the low voltage end 33 of each capillary 20 is in contact with buffer 30 in container 32. Buffer 30 is at ground potential in this embodiment. A sample to be analyzed is injected into each capillary 20 at the high voltage end 13. The samples migrate through the array 23 of individual capillaries 20 and flow out of the low voltage end 33 of each capillary 20 into buffer 30.

For the sake of simplicity, the voltage source equipment for applying the high potential to the capillaries is not shown. In this embodiment, the high potential end of the capillary electrophoresis system is at the entrance end of the capillary. Herein, the high voltage end of each capillary is also referred to as the intake end, and the low voltage end as the outflow end. For specifics regarding a description of the components and operation of capillary electrophoresis systems, see, for example, H. Swerdlow et al., Anal. Chem., 63, 2835–2841 (1991).

The system also includes a bundle 10 of optical fibers 15 wherein each optical fiber 15 is coupled to an individual capillary 20 by insertion into the outflow end 33 of the capillary 20. Each optical fiber 15 has a first end 42 and a second end 70. Excitation laser 40 is coupled into the individual optical fibers 15 of bundle 10 at first ends 42 by means of a microscope objective 45. First ends 42 of the fibers are distal to the capillaries 20. The laser 40 and the microscope objective 45 are positioned so that the laser beam, represented by arrow 47, is focused onto the ends 42 of the optical fibers 15. The capillaries 20 with optical fibers 15 inserted at the outflow ends 33 of the capillaries 20 are arranged in an array 102, which is held in a fixed position on a stage 52 under an objective 65 of a microscope 60. The capillaries 20 as well as the optical fibers 15 are held firmly in place in an array 102 by guides (not shown). The fluorescent light emitted from the fluorescent species in the array 102 of capillaries 20 through capillary walls 104 is imaged orthogonally through the microscope 60 by means of an adapter 55 onto a charge-coupled device camera 50 for signal analysis.

FIG. 2 (not to scale) shows the array 102 of capillaries 20 with optical fibers 15 inserted at the outflow end 33 of the capillaries 20 in capillary electrophoresis. The outflow end 33 of the capillaries 20 are aligned substantially evenly in the field of the microscope 60. Optical fibers 15 are positioned into the capillaries 20 so that the second ends 70 of the optical fibers 15 are also aligned substantially evenly. Capillaries 80 with black coating are placed between each of capillaries 20 that are used for separation, to act as spacers for reducing the crosstalk between the separation capillaries 20. Detection zone 90 is the area of a capillary 20 before the end 70 of the optical fiber. The detection zones 90 of the capillaries 20 are arranged such that the capillary images are detected by the pixel columns of the camera 50 (not shown) coupled to the microscope 60.

Referring again to FIG. 1, the microscope objective 45 is a means for collimating the laser beam 47 onto the ends of a plurality of optical fibers 15. Depending on the power of the laser 40, the diameter of the laser beam 47, and the number and size of the optical fibers 15, the collimating means 45 can either be focusing or diverging the laser beam 47 to irradiate the ends 42 of the optical fibers 15. If the laser has a narrow beam of high power and the number of optical fibers is large, the microscope objective 45 can be used to diverge and spread the laser beam 47 evenly over the ends 42 of the optical fibers 15. If the laser 40 has a wide beam 47 of low power, it may be necessary to use the microscope objective 45, to focus the beam 47 onto the ends 42 of the optical fibers 15.

The light source used for excitation of the fluorophores in the samples of interest is a means for generating a coherent light, or a laser. The wavelength of the laser radiation is selected to match the excitation wavelength of the particular fluorophore. Suitable fluorescent species typically absorb light at a wavelength of about 250–700 nm, preferably about 350–500 nm, and emit light at a wavelength of about 400–800 nm.

Preferably a laser that can deliver about 0.05–10 mW per fiber, and more preferably about 0.1–0.5 mW per fiber is used, although lasers with power outside these ranges can be employed. Any appropriate laser of the proper wavelength and energy can be used. A commonly used laser is an Argon laser that produces coherent light of 488 nm. Such lasers are commercially available from, for example, Cyonics of San Jose, Calif.

Any appropriate optical fibers can be used for illuminating the samples in the capillaries. Optical fibers are selected based on cost, size, and the attenuation of light intensity related to length. Most typical commercial optical fibers of the appropriate diameter are suitable. The selection of the size of the optical fiber is dependent on the capillary inside diameter (i.d.). The fibers should be small enough to facilitate smooth insertion into the capillaries. The fibers should not be so large, however, that they hinder substantially the flow of analytes and buffer in the capillaries. Preferably, the reduction of flow rate due to the presence of the optical fiber is less than about 50%. Generally the size of the optical fiber is not critical as long as the detection zone is well irradiated. The fibers and the capillaries are held in place by guides. Generally, however, the friction between the fiber and the capillary is adequate to affix the fibers in place so that fluid motion or minor vibration does not cause a fiber to move in relation to the capillary. Although in this embodiment each capillary is coupled to one optical fiber, more than one fiber can be used to irradiate each capillary. There can be a slight pressure differential because of the restricted cross section of the capillary bore. Therefore, the overlap region should be short compared to the length of the capillary. Typically, the overlap is about 0.1–2 cm. Optical fibers are commercially available from, for example, Edmond Scientific Co., Barrington, N.J. The insertion of an optical fiber to the end of the capillary reduces contributions from the surfaces of the optical fiber to the separation.

Capillaries are often coated with a polymer, typically polyimide. In fluorescence detection, the capillary wall and the polyimide coating fluoresce if they are irradiated by the laser light. In certain cases, this may interfere with the small fluorescence signal from the analytes. Thus, the preferred embodiment of the present invention focuses the excitation laser beam directly into the capillary core axially by focusing the laser beam into an optical fiber, which has been inserted into the separation capillary. Because of the unique light transmitting property of the optical fiber, light is efficiently transmitted to the liquid core.

Although the preferred embodiment is to irradiate the sample axially, a viable application of the present invention is to irradiate orthogonally, i.e., perpendicular to the capillary 20 length. The illuminating ends of the optical fibers 15 are located on the opposite side of the array 102 of capillaries 20 in relation to the microscope 60 and the camera 50. Optical fibers 15 are again coupled individually to the capillaries 20. FIG. 3 (not to scale) illustrates this scheme. A camera 50 (not shown) is coupled to a microscope objective 65 in substantially the same manner as in FIG. 1 for detecting fluorescence. Optical fibers 15 are oriented at an angle that is perpendicular to capillaries 20 but is 45° in relation to the light path between the capillaries 20 and the microscope objective 65. (For the purpose of simplicity, the electrophoretic equipment, camera, laser and microscope body are not shown. They can be the same as in FIG. 1.) Again, as in the previously described embodiment, the capillaries 20 as well as the optical fibers 15 are held by guides (not shown in FIG. 3) and affixed in place to prevent movement. Although 45° is preferred, the angle of incident light on the surface of the capillary 20 can be varied as long as care is taken to reduce stray laser light from interfering with the fluorescent light as detected by the camera. Although not shown in FIG. 3, spacers similar to those in FIG. 2 can be used for reducing stray light. The size of the optical fiber 15 can be selected so that the fibers 15 and spacers 80 may be conveniently held in place.

The laser/capillary interface of individually coupling optical fibers to capillaries 20 represented by FIG. 3 is also advantageous because alignment of the optical fiber 15 with the laser beam 47 can be made permanent. Changing the separation capillary is then simplified. With fibers or capillaries of larger than 50 μm, alignment does not even require the use of a microscope. Because there is no moving part, once the alignment is made, no further alignment is needed. Single-mode optical fibers with diameters down to 5 μm are presently available. Therefore capillaries with inside diameters of slightly larger diameters may be utilized in electrophoresis.

The emitted fluorescent light that passes through the capillary wall 104 is detected by a charge transfer device imaging system 50 through coupling with a microscope 60. Any appropriate microscope or camera lens system may be used so long as it adequately transmits the image of the separation zone of the capillary array to the imaging camera.

A Bausch and Lomb Stereo Zoom 7 binocular microscope with camera extension is suitable.

The present invention is capable of multiplexing more than 1000, e.g., 1024, capillaries in, for example, a DNA sequencing run. This number is based on the number of column elements already available in modern solid-state imaging devices. The principle is the same as an embodiment of an optical system device based on 10 capillaries. Fiber bundles with up to 1000 fibers are readily available at a low cost.

For an embodiment of 1024 capillaries, an argon ion laser of 1–5 Watt power or any appropriate laser of suitable power and wavelength can be used to illuminate one end 42 of the fiber bundle, conveniently distributing about 0.4–2 mW of light to each fiber. The other end 70 of the fiber bundle 10 can be fanned out into a flat sheet on a guide (not shown), which is a set of parallel grooves to fix the location of each fiber 15 to maintain a constant spacing. Similarly, 1024 separation capillaries can also form a flat sheet on a suitable guide. Insertion of the fibers 15 (smaller than 50 μm) into the capillaries 20 (about 75 μm i.d.) as in the preferred embodiment, or positioning the optical fibers 15 at a 45° angle to the capillaries 20 as in another embodiment, can be readily accomplished. The imaging optics 50 can be a standard distortion-free camera lens, matching each of the optical windows on the capillaries 20 to each pixel column on the detector. Several rows of pixels can be binned, i.e., the data are added together before transferring to storage, to provide increased dynamic range without degrading resolution. The data rate of CCD cameras, even in the high-sensitivity, slow-scan mode, can be around 10 Hz. Since all channels are monitored at all times, true multiplexing is achieved.

Both charge injection devices (CID), and charged coupled devices, (CCD), are charge transfer devices (CTD) containing semiconductor material. In a CTD, an individual detector contains several conductive electrodes and a region for photogenerated charge storage. A photon striking the semiconductor material in the device creates a mobile hole which is collected as a positive charge under an electrode. The number of photons striking the device is counted by transferring the charges. In the CCD, the charge from each detector element is moved to a charge sensing amplifier by sequentially passing the charge from one detector element to the next adjacent detector element. The CCD is designed in such a way that it is necessary to shift through all the detector elements in the entire detector before proceeding to the next exposure. As a consequence, the reading of data in a CCD detector cannot be done in a random access manner. However, the amplifier gives a very high signal to noise output.

In a CID, there are two different kinds of electrodes, a collection electrode and a sense electrode. The photogenerated charge is kept in the detector element by potential barriers that prevent the charge from migrating along the electrode. The charge that is kept at the collection electrode can be transferred to the sense electrode. This transfer induces a voltage change on the sense electrode which can be measured. Thus, during the readout process, the charge is not altered in the detection element. This nondestructive readout enables a random access to the charge stored in the detector elements. In CID, the nondestructive reading of charge can be analyzed by a computer system to determine the proper process exposure time for each emission line of the spectrum. Therefore, data rate can be increased. Data storage is also substantially reduced because the information can be evaluated before binning or reading multiple frames, which is a way of reducing background noise by summation of data from multiple measurements. Also, once a base of a DNA molecule is identified, the other 3 lanes in the set of 4 need not be read or subjected to data processing to analyze for the other three bases. Imaging design can also include color filters to accommodate the advanced techniques such as the 4-color sequencing process utilizing different parts of the CID detector. For references for CID and CCD, see J. V. Sweedler et al., Anal. Chem., 60, 282A–291A (1988), and P. M. Apperson et al., Anal. Chem., 60, 327A–325A (1988).

A wide range of fluorescence labels can be used. A researcher would be able to select the proper label for the particular target species and the fluorescence system used. Common fluorescence labels include materials such as salicylate, 3,3'-diethylthiadicarbocyanine iodide (DTDCI), dansyl chloride, fluorescein, fluorescein isothiocyanate, ethidium bromide, rhodamine, and the like. Commonly used fluorescent dyes that can be used for tagging target species include FAM, JOE, TAMRA, which are rhodamine derivatives. Such dyes are commercially available from, for example, Applied Biosystem, Foster City, Calif.

Capillary Electrophoresis

In capillary electrophoresis, a buffer filled capillary is suspended between two reservoirs filled with buffer. An electric field is applied across the two ends of the capillary. The electrical potential that generates the electric field is in the range of kilovolts. Samples are typically introduced at the high potential end and under the influence of the electrical field. The same sample can be introduced into many capillaries, or a different sample can be introduced into each capillary. Typically an array of capillaries are held in a guide and the intake ends of the capillaries are dipped into vials that contain samples. Obviously each vial can contain the same or different samples as the other vials. After the samples are taken in by the capillaries, the ends of the capillaries are removed from the sample vials and submerged in a buffer which can be in a common container or in separate vials. The samples migrate toward the low potential end. When the samples leave the capillary zones after migrating through the capillary, they are detected by a detector. Techniques for capillary electrophoresis are well known in art. The above-mentioned references, such as Huang et al, Yeung et al., Zare et al., and Baba et al., are illustrative of the exemplary equipment and procedures for such techniques.

The channel length for capillary electrophoresis is selected such that it is effective for achieving proper separation of species. Generally, the longer the channel, the greater the time a sample will take in migrating through the capillary and thus the species may be separated from one another with greater distances. However, longer channels would also contribute to the band broadening and lead to excessive separation time. Generally, for capillary electrophoresis, which includes CZE and CGE, the capillaries are about 10 cm to about 5 meters long, and preferably about 20 cm to about 200 cm long. In capillary gel electrophoresis, the more preferred channel length is about 10 cm to about 100 cm long.

The capillaries should be constructed of material that is sturdy and durable so that it can maintain its physical integrity under repeated use under normal conditions for capillary electrophoresis. It should be constructed of nonconductive material such that high voltages can be applied across the capillary without generating excessive heat. It is also necessary that part of the capillary be translucent so that the fluorescent light that is emitted by the fluorescent species can be transmitted across the capillary wall to the detection system. Inorganic materials such as quartz, glass, fused silica, and organic materials such as teflon (polytetrafluoroethylene and fluorinated ethylene/propylene polymers), polyfluoroethylene, aramide, nylon (polyamide), polyvinyl chloride, polyvinyl fluoride, polystyrene, polyethylene and the like may be used. The capillary is translucent to light of a wavelength of about 200–1,500 nm, preferably about 350–800 nm. In a case where the capillary is not translucent to such light, the detection zone of such a capillary is preferably made of material that is translucent to such light.

To achieve total internal reflection, the choice of the electrophoretic buffer may have to be limited. A buffer with a lower refractive index is employed to provide total reflectance. Materials other than fused silica may be used for the separation capillary so that such buffers with lower refractive indices may be applicable.

One distinct advantage of the axial-beam technique (as represented by FIGS. 1 and 2) is that it allows the supportive coating on the capillary to remain intact. Most fused silica capillaries have a polyimide coating that is known to emit a broad fluorescence when exposed to wavelengths of light under 600 nm. If a through-the-wall excitation scheme (as represented by FIG. 3) is used without first removing this coating the fluorescence background may mask the weak analyte signal at low concentrations. It is therefore preferable that the detection zone of the capillary has no coating. The polymer coating may be removed by any method known in the art, for example, by boiling in sulfuric acid for a period of time.

In electrophoresis, the buffer is typically selected so that it would aid in the solubilization or suspension of the species that are present in the sample. Typically such a liquid, an electrolyte, which contains both anionic and cationic species, contains about 0.005–10 moles per liter of ionic species and preferably about 0.001–0.5 mole per liter of ionic species. Examples of an electrolyte for a typical electrophoresis system are mixtures of water with organic solvents and salts. Representative material that can be mixed with water to produce appropriate electrolytes includes inorganic salts such as phosphates, bicarbonates and borates, and organic acids such as acetic acids, propionic acids, citric acids, chloroacetic acids and their corresponding salts and the like; lower alkyl amines such as methyl amines, lower alcohols such as ethanol, methanol, and propanol; lower polyols such as the lower alkane diols; nitrogen containing solvents including acetonitrile, pyridine, and the like; lower ketones such as acetone and methyl ethyl ketone; and lower alkyl amides such as dimethyl formamide, N-methyl and N-ethyl formamide, and the like. The above ionic and electrolyte species are given for illustrative purposes only. A researcher would be able to formulate electrolytes from the above-mentioned species and in combination with other species such an amino acids, salts, alkalies, etc. to produce suitable support electrolytes for using capillary electrophoresis systems.

Reducing Interference

In the present invention, light may be propagated through a capillary by partial or total internal reflection. The invention is equally applicable to either case. In total internal reflection, no stray light from the quartz wall or the polyamide coating reaches the camera. Total internal reflection is advantageous in certain fluorescence excitation applications because all the light entering the capillary within a certain critical angle will propagate with little loss. This results in less noise due to capillary misalignment and a detector response that should be independent of the location of the analyte band. The capillary can thus be bent without attenuating the excitation beam. An added advantage in axial-beam fluorescence excitation with total internal reflection is that there is very little (in principle, none) scattered light originating from the capillary wall. This should allow the use of capillaries with intact polyimide coatings without problems of interference due to absorption or greatly increased fluorescence background, Another benefit from the axial-beam geometry is a longer absorption path length compared to irradiation across the capillary. This increases the interaction length from 75 μm to 1 mm to provide increased fluorescence intensity.

Increased laser power is advantageous in providing a larger analyte signal. However, fluorophores are easily bleached, i.e., their fluorescing characteristic destroyed, by the laser beam, even at the milliwatt level, negating any increase in excitation intensity. Furthermore, in the axial-beam arrangement, fluorophores may be completely bleached before they reach the detection zone because of the residence time in the excitation beam. A novel way to increase the incident laser power without bleaching the compounds of interest is to add an inert absorber that does not react chemically with the sample or the buffer contained in the capillary. Suitable absorbers include Orange G, Cresol Red, or any other nonfluorescing dye molecules. In a capillary containing an absorber producing an absorbance of 0.6 per cm of path length, for example, the incident laser intensity is reduced to 50% in 5 mm, typically the distance between the end of the optical fiber and the detection zone. Over a distance of about 4 cm, light intensity is reduced to less than 0.5% of its original value. Thus if a detection device is placed close to the point where excitation light is introduced, an analyte band traveling from the opposite end of the capillary will interact with very little light until it is near the detection zone. Therefore photochemical bleaching is greatly reduced. It may be necessary to isolate the detection zone from the end of the optical fiber, however, so that specular reflection and fluorescence from the fiber can be discriminated against.

In the case of partial internal reflection, only a small fraction of the incident laser intensity generally remains in the capillary after 1 cm of travel. A small bend can be made in the capillary after the detection region to prohibit any further light travel. This renders the use of an organic absorber unnecessary, because in partial internal reflection, the incident laser light exits the capillary at the bend.

Because interested bands of analytes are not passing by the detection zone continuously, an expert system can be used to predict when the bands are approaching the detection zone. Only during such time where the bands are near to the detection zone would the laser irradiation be needed.

An additional electronic shutter in the beam path may be used to open synchronously with the CCD shutter, allowing light to be transmitted to the capillary only during the period of data collection, and blocking the incident beam during the time when no signal is collected. With the implementation of an expert system for data collection only when interested data is being produced, signal collection time and thus photochemical damage can be greatly reduced.

Figure 4:
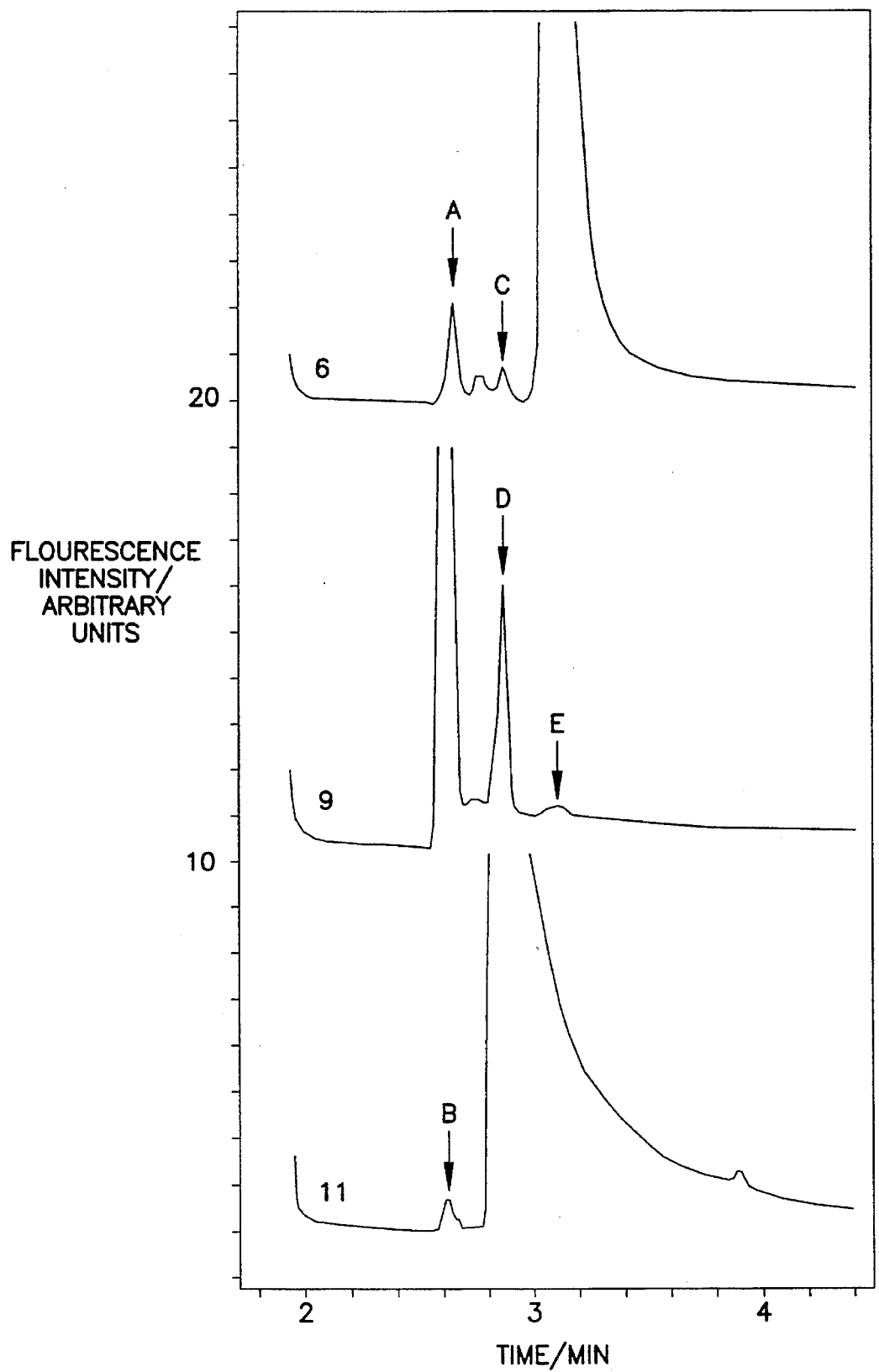
FIG. 4 Shows graphs of fluorescence intensity versus time in three different capillaries. These graphs show crosstalk between separation channels in the absence of spacers. The eluted fluorophore is 3,3'-diethylthiadicarbocyanine iodide (DTDCI). The elution times are different in the three graphs due to variations among the capillaries. The scale is deliberately magnified.
Figure 5A:
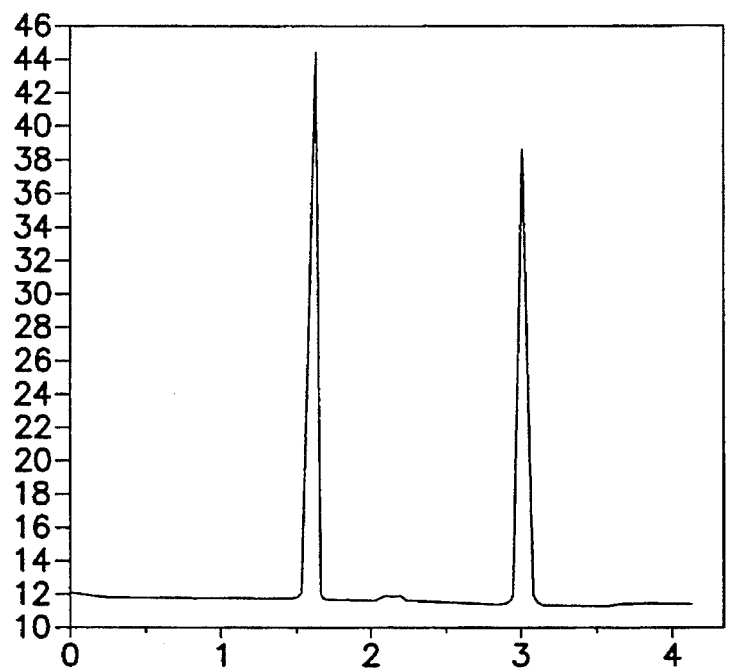
FIG. 5 shows graphs of fluorescence signals from 10 different capillaries. These graph show the results of simultaneous electrophoretic separations of riboflavin and fluorescein. The concentrations of riboflavin and fluorescein were $5 \times 10^{-5}$ M and $6 \times 10^{-7}$ M, respectively. The injection time at 7500 volts was 5 seconds. The time axis is in minutes.
Figure 5B:
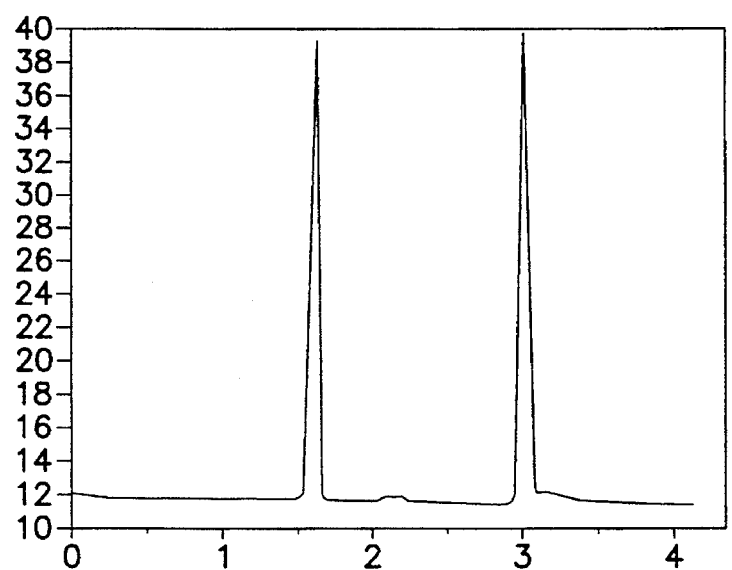
Figure 5C:
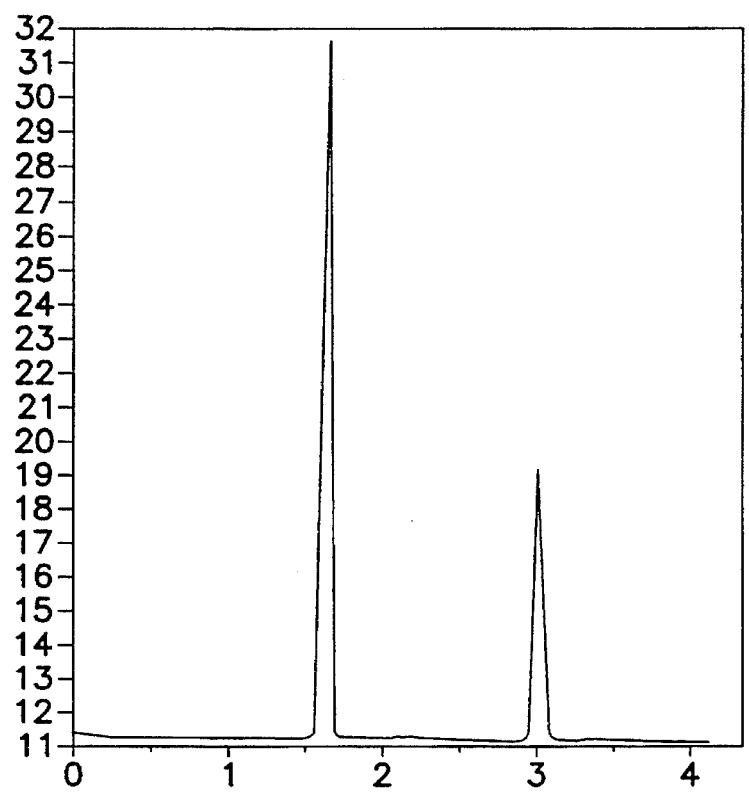
Figure 5D:
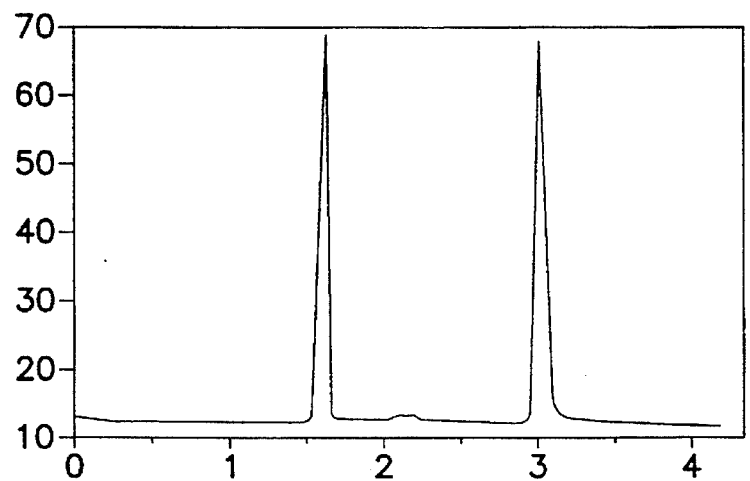
Figure 5E:
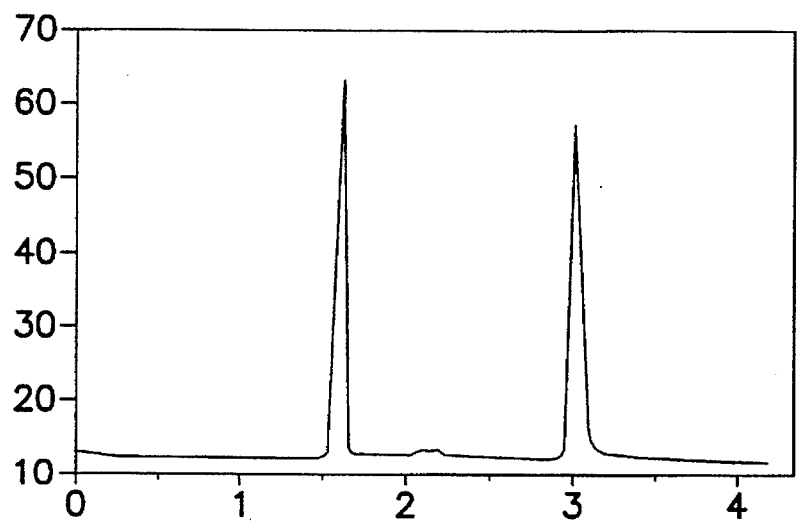
Figure 5F:
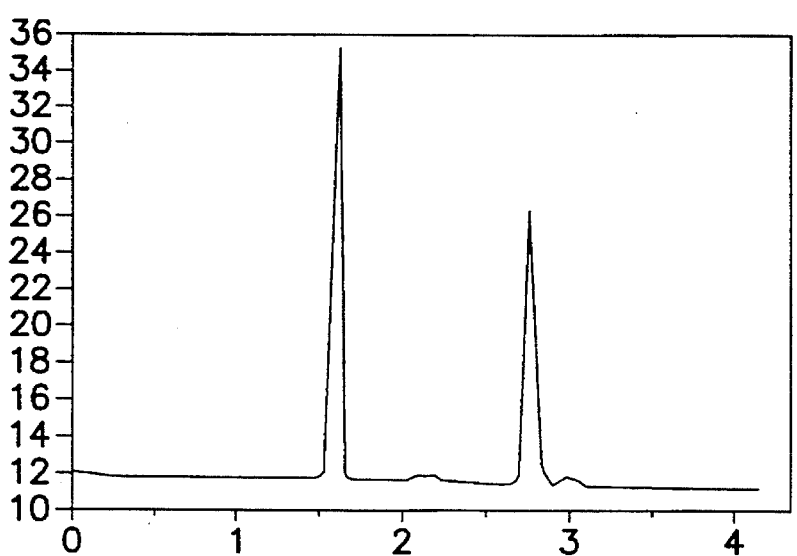
Figure 5G:
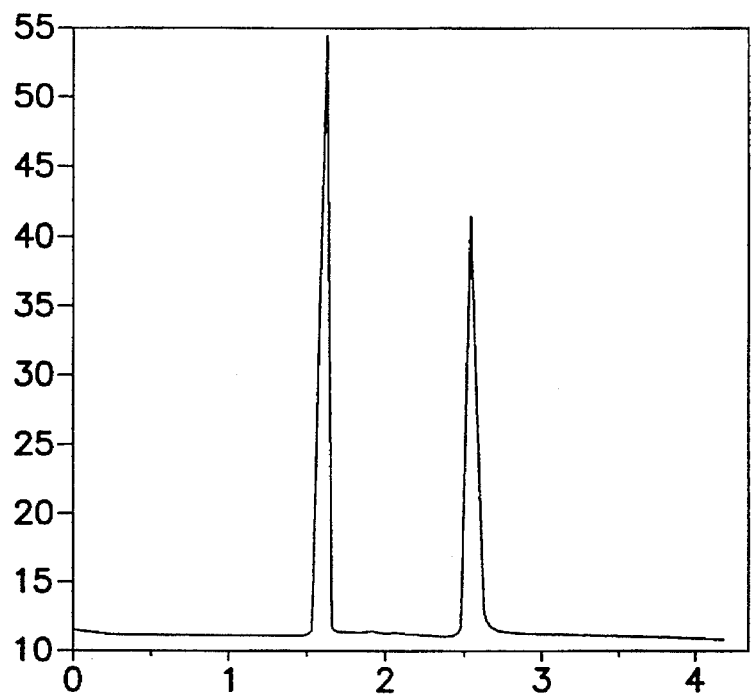
Figure 5H:
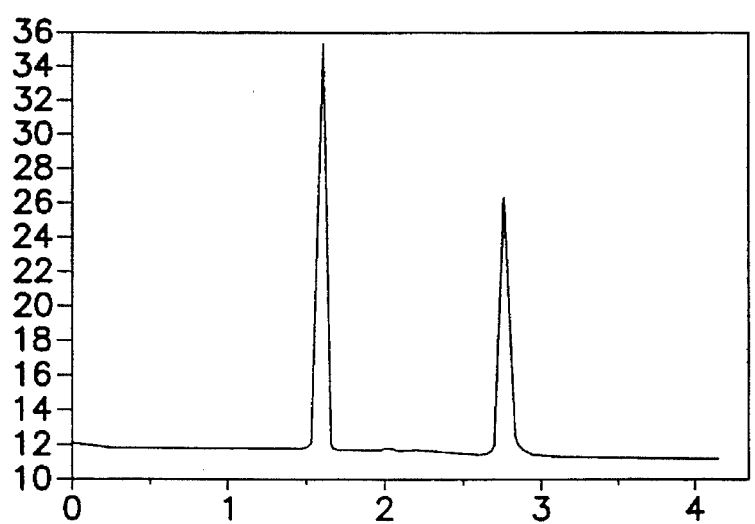
Figure 5I:
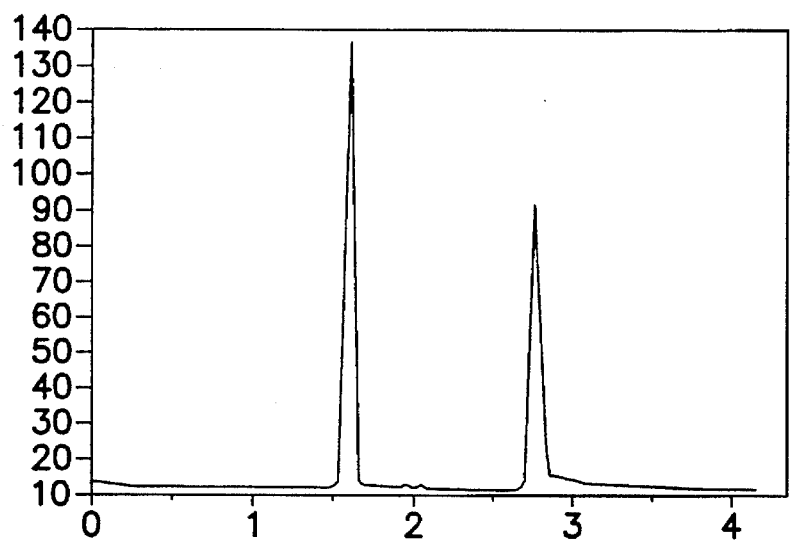
Figure 5J:
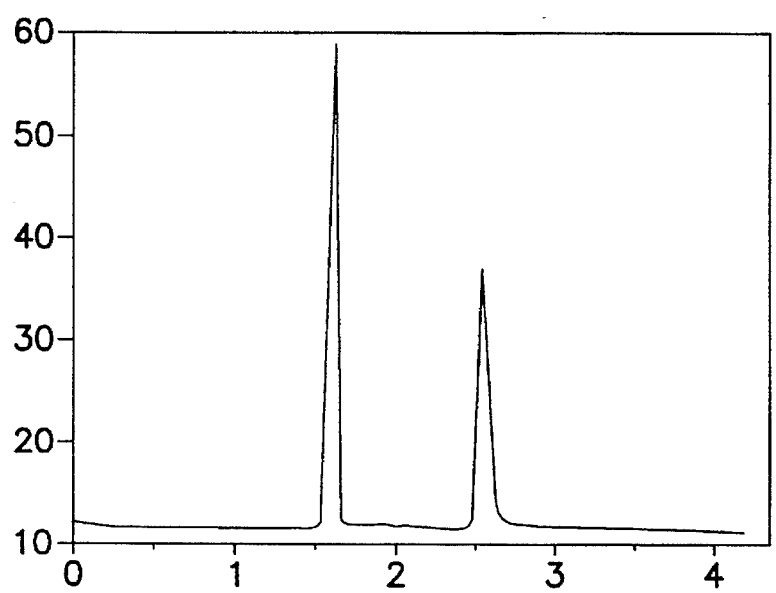

Crosstalk between the separation channels is another important design consideration in multiplexed detectors. This is the interference of the fluorescence between neighboring capillaries. Such interferences must be eliminated or reduced to an acceptable level before applications such as DNA sequencing can be practiced. Crosstalk has two causes: signal light reflections from the walls of adjacent capillaries and scattered light from optics inside the microscope. When capillaries are placed side by side, false peaks are observed in nearby capillaries. FIG. 4 shows such false peaks. In FIG. 4, the tracings are derived from electropherograms of capillaries No. 6, 9, and 11 of an array of thirteen separation capillaries. Peaks A and B are reflections of the fluorescence signal in capillary 9. C and D arise from the signal in capillary 11, and E represents interference from capillary 6. Crosstalk can be reduced by placing spacers, which are the same 150 µm outside diameter (o.d.) capillaries coated with black ink, between each of the separation capillaries. Such black capillaries are illustrative examples. Other suitable spacers may certainly be devised using the above principle.

The fluorescence, once imaged onto the CCD camera, is extracted from the memory of the CCD camera and analyzed using a computer. A knowledgeable person will be able to select the proper software, computer program and algorithm for the analysis of the data. Such data may also be used for the control of the electrophoresis system or the detection system. For example, valves or pumps may be operated by control signals generated by the computer based on the analysis of the capillary electrophoresis results.

Proper calibration methods can be used to compensate for slight variations in migration times from one capillary to the next. An example of such a method is the utilization of a migration index as described in T. T. Lee et al., Anal. Chem. 63, 2842–2848 (1991). This method involves separate current measurements in each capillary. If series resistors are connected to each of the capillaries, the resulting voltage can be monitored sequentially by an A/D converter and a desktop computer. Measurements every 0.1 second are sufficient for calibration compensations. Even for 1000 capillaries, using commercially available serial interface boards, such calibration would still be a relatively simple task. A knowledgeable person would be able to configure computers and electronic components, and utilize software systems to compensate for variations by proper calibrations.

The present invention maybe used for the separation and measurement of the species present in samples of biological, ecological, or chemical interest. Of particular interest are macromolecules such as proteins, polypeptides, saccharides and polysaccharides, genetic materials such as nucleic acids, polynucleotides, carbohydrates, cellular materials such as bacteria, viruses, organelles, cell fragments, metabolites, drugs, and the like and combinations thereof. Protein that are of interest include proteins that are present in the plasma, which includes albumin, globulin, fibrinogen, blood clotting factors, hormones, and the like. Other interesting proteins which may be separated using the capillary electrophoresis systems are interferons, enzymes, growth factors, and the like. Of particular interest are the group of macromolecules that are associated with the genetic materials of living organisms. These include nucleic acids and oligonucleotides such as RNA, DNA, their fragments and combinations, chromosomes, genes, as well as fragments and combinations thereof. Other chemicals that can be detected using the present invention include, but is not limited to: pharmaceuticals such as antibiotics, agricultural chemicals such as insectisides and herbicides.

The proper selection of the capillary electrophoresis system is important for the separation of the species in the samples. An important factor to be considered is the plugging of the system. For example, samples containing cell fragments or cells such as bacteria, large chromosomes, DNAs, RNAs may result in the plugging of capillaries containing gel in capillary gel electrophoresis. A scientist would be able to select the proper capillary electrophoresis system for the particular species of interest. The present invention is equally applicable to capillary gel electrophoresis (CGE), wherein a gel or a similar sieving medium is present in the capillaries, and capillary zone electrophoresis (CZE), wherein no gel is used. Depending on the particular target species, different electrophoresis systems may be used. Details about the selection of proper channel size, channel length, material construction for the capillaries, solvents, electrolytes, gels, etc. may be varied by the person conducting the analysis.

Several important advantages are realized by the present invention. First, truly simultaneous multiplexing of capillary electrophoresis can be achieved because the CCD camera monitors all capillaries simultaneously, resulting in data rates fast enough for sequencing at greater than about 1 nucleotide, i.e., base, per second per lane. This translates to 1000 bases per second for a system with 1000 capillaries, which already meets the goal of sequencing rate necessary for the Human Genome initiative. Second, there are no moving parts and the injection (high voltage) end of the capillary bundle can be freely manipulated without affecting alignment. Third, the 5 mW excitation laser simply irradiates the entrance of the optical fiber bundle without critical alignment of the optics to achieve distribution of energy into each capillary. Fourth, although there are variations in the excitation energies reaching each capillary, these variations can be compensated for by calibration in the same way the individual CCD pixels are normalized. Fifth, the variations in absolute and relative migration times for the target compounds can be adjusted for by using a migration index and an adjusted migration index. Sixth, variations in the relative peak heights and areas among the capillaries for the same injected sample concentration can be corrected by the T. T. Lee et al., Anal. Chem. 63, 2842–2848 (1991) calibration method to reduce the bias to less than 5%, which is adequate for DNA sequencing.

The following examples are offered to further illustrate the various specific and preferred embodiments and techniques. It should be understood, however, that many variations and modifications may be made while remaining within the scope of the present invention.

EXAMPLES

Example 1

Excitation

A schematic diagram of the multiplexing apparatus is shown in FIGS. 1 and 2. Approximately 500 optical fibers (0.0051 cm o.d., P31735, Edmond Scientific, Barrington, N.J.) were grouped together and inserted into a 0.32 cm i.d. heat shrinking tube. After heating, a razor blade was used to cleave the heat shrink casing and the enclosed fibers. This fiber bundle was inserted into the laser beam path by a microscope objective (Bausch and Lomb, Rochester, N.Y. 16 mm, 10X, BM2888). The 488 nm laser beam (2011-30SL, Cyonics, San Jose, Calif.) was partially focused by the objective to provide a beam spot size that overlaps the desired number of fibers in the illumination zone. A total laser power of 5 mW was thus divided among 10–12 optical fibers. The free end of each illuminated fiber was inserted. 1.5 cm into a different fused silica capillary as discussed previously.

Detection

The capillary array in the detection region was imaged onto a charge-coupled device (CCD) camera (Photometrics, Tucson, Ariz., Series 200) through the camera extension of a binocular microscope (Bausch and Lomb, Stereo Zoom 7). Each of the optical windows on the capillaries was matched to a pixel column of the camera. The CCD camera was operated in a 25 to 1 column binning mode. This allowed compression of 200 columns and 375 rows of image data into an 8×375 array. Data extraction from the CC200 memory and analysis was carried out on a PC-compatible 80386-based computer equipped with an IEEE interface. Each frame of data, corresponding to a 0.1 second CCD exposure taken every 0.9 second, was stored in an individual file. The total storage space for the 400 data files collected during a run was under 4 megabytes. Using a simple BASIC algorithm, the intensities of selected 3×5 element regions representing each separation capillary were summed. These time dependent sums were then plotted as electropherograms.

Separation

Silica capillaries (Polymicro Technologies, Phoenix, Ariz., 75 μm i.d., 150 μm o.d., #TSP075150, length=27 cm) were prepared by removing 1 cm of polyamide coating with boiling sulfuric acid 25 cm from the injection end. Equilibration consisted of flushing with 0.1 M NaOH followed by filling with running buffer (10 mM bicarbonate adjusted to about pH=9) and applying a 5 kV potential for at least 10 hours prior to fiber insertion. Solutions of riboflavin (Bio-Rad) and fluorescein (Eastman Kodak) were prepared in running buffer. The electrophoretic separation was driven at +7.5 kV using a high voltage power supply (Glassman, Whitehouse Station, N.J., model PS/MJ30P0400-11) with a platinum electrode at the high voltage end and a chrommel electrode at ground. Injection of samples was by the standard method by placing the intake ends of the capillaries in a sample container. When injection of sample is complete, the capillaries were removed from the sample container and placed in the buffer reservoir.

Other Techniques Employed

In the present case, with partial internal reflection, only a small fraction of the incident laser intensity remained in the capillary after 1 cm of travel. A small bend was made in the capillary after the detection region to prohibit any further light travel. This obviated the need for an organic absorber. An additional electronic shutter in the beam path, which opened synchronously with the CCD shutter, blocked the incident beam during the 80% of time when no signal was being collected. This greatly reduced photochemical damage in the detection region. The lack of photochemical bleaching was confirmed by comparing peak heights in single capillaries with different amounts of cumulative exposure to laser excitation.

To reduce crosstalk, spacers, which were the same 150 μm o.d. capillaries coated with black ink, were placed between each of the separation capillaries. Thus crosstalk was reduced to well below 1% of the observed signal.

Results

Electropherograms for ten parallel separations of riboflavin and fluorescein are shown in FIG. 5. The retention times for the two components were similar to those in control experiments (not shown). This indicated that the electroosmotic flow normally present in an open capillary is not significantly disturbed by fiber insertion. The individual retention times in the 10 capillaries varied noticeably. The relative standard deviations (RSD) for the migration times of riboflavin ($t_1$) and for the migration times of fluorescein ($t_2$) were about 3% and 5.5% respectively. Since the 10 capillaries were unrelated, even the relative migration times of fluorescein ($t_2/t_1$), showed a 4% RSD. The calculated mobilities ($\mu$) of fluorescein (related to $1/t_2-1/t_1$) gave an RSD of 5%. Repeat experiments showed similar results. This range of RSD was the result of the uncontrolled nature of the surfaces inside each capillary, variations in capillary i.d., variations in fiber-optic o.d., and differences in the length of insertion of the fiber. However, for a given capillary, run-to-run reproducibility was good. The ranges of RSD for $t_1$, $t_2$, $t_2/t_1$, and $\mu$ are 0.4% to 1.1%, 0.4% to 3.4%, 0.4% to 2.4%, and 0.4% to 2.4% respectively. These were similar to typical run-to-run variations in capillary electrophoresis in the absence of temperature control and for constant voltage operation.

FIG. 4 also shows large variations in the peak areas among the 10 parallel capillaries. The RSD ranged from 70% for riboflavin ($A_1$), 95% for fluorescein ($A_2$), and 29% for the relative areas ($A_2/A_1$). Large differences are expected due to nonuniform coupling of excitation energy into each capillary and variations in pixel sensitivities across the CCD. These dominated over the variations of individual capillary surfaces and geometries. For a given capillary, run-to-run (RSD ranges) for $A_1$, $A_2$, and $A_2/A_1$ was 6% to 28%, 6% to 29%, and 3.6% to 17% respectively. Injection bias was responsible for these variations. These were more pronounced than variations in migration times because factors such as unequal time constants for electromigration injection, ubiquitous injection, and the particular characteristics of the capillary entrance affected the injected amount but not the migration times. It is interesting to note that the peak areas were not correlated with the migration times. This indicated that photochemical bleaching was not important in these experiments. These variations should not be considered as shortcomings of the present invention because they would be present in conventional capillary electrophoresis systems. Moreover, these variations can be corrected by proper calibration procedures. Also, internal standards for each of the unknowns in the sample can be used for proper calibrations. For a discussion on the significance of the RSDs and calibration, see T. T. Lee et al., Anal. Chem., 64, 1226–1231 (1992).

Example 2

In this example, a DNA sequencing experiment similar to Huang's is done. See, X. C. Huang et al., Anal. Chem., 64, 967–972 (1992). One hundred capillaries are to be used. Zero-cross-linked polyacrylamide gel-filled capillaries are prepared using a procedure described by Cohen et al., Proc. Natl. Acad. Sci., U.S.A., 85, 9660–9663 (1988). A detection window is made on the capillary near to the exit end by removing the polyimide coating with boiling in sulfuric acid as in Example 1. The inner wall of the capillaries is then treated with a bifunctional reagent and then vacuum siphon filled with a gel solution as described by Huang. Chain-terminated M13mp18 DNA fragments are made with fluorescein-tagged primer (FAM, Applied Biosystems, Foster City, Calif.) as described by M. A. Quesada et al., BioTechniques, 19(10), 616–625 (1991).

The same type of capillaries and optical fibers as Example 1 are used. Optical fibers are inserted into the capillaries in the same manner as in Example 1. The fibers are inserted to such a distance (about 0.5 cm) inside the capillaries so that the fluorescent light may be readily detected by the detection system. A 50 mW laser generating 488 nm light is used. The size of the capillary and the fiber, the equipment and operation of the electrophoresis system, and the detection system are as described in Example 1.

Example 3

In this example, DNA sequencing is done in the same manner as in Example 2. The irradiation of the samples, however, is orthogonal rather than axial. As is shown in FIG. 3, the illuminating ends of the optical fibers are on the side of the array of capillaries that is away from the microscope and the camera. Again, the outside diameters the capillaries are 150 microns. Optical fibers of 50 microns are used. The optical fiber is oriented at an angle that is perpendicular to the length of the capillary but is 45° in relation to the light path between the capillary and the camera. The same equipment as in Example 2 is used for the electrophoresis, coherent light generation, and imaging.

All patents, patent documents and publications cited hereinabove are incorporated by reference herein. All percentages given are weight percents except indicated otherwise.

What is claimed is:

1. A multiplexed method of detecting the presence of macromolecules in samples present in a plurality of capillaries in capillary electrophoresis comprising:
   (a) providing a buffer solution containing a fluorophore;
   (b) introducing samples into a plurality of capillaries in a capillary electrophoresis system, each capillary containing the buffer; and
   (c) substantially simultaneously irradiating the samples in the capillaries with coherent light to cause fluorescence.

2. The method of claim 1 wherein the coherent light is transmitted through optical fibers individually coupled to the capillaries.

3. The method of claim 1 wherein the step of substantially simultaneously irradiating comprises irradiating through the wall of each capillary.

4. A multiplexed method of detecting the presence of macromolecules in samples present in a plurality of capillaries in capillary electrophoresis, comprising the steps of:
   (a) providing a buffer solution containing a fluorophore;
   (b) introducing samples into a plurality of capillaries in a capillary electrophoresis system, each capillary containing the buffer;
   (c) irradiating each sample in each capillary to cause fluorescence of the macromolecule; and
   (d) substantially simultaneously detecting changes in fluorescent emission.

5. The method of claim 4 wherein the step of substantially simultaneously detecting comprises detecting fluorescent emission through the wall of each of the capillaries by the fluorescent species.

6. A multiplexed fluorescence detection system for use with capillary electrophoresis to detect target species in samples comprising:
   (a) an array of at least two capillaries each having an intake end, an outflow end, an inside diameter of about 40–100 microns, and an annular wall wherein at least a portion of the wall is translucent to light having a wavelength of about 200–1,500 nm, the intake end being in fluid communication with a sample so that the sample is drawn into the capillary;
   (b) means for irradiating each sample in each capillary to cause fluorescence of the target species; and
   (c) means for substantially simultaneously detecting changes in fluorescent emission.

7. The detection system of claim 6 wherein the capillary array comprises at least about 100 capillaries.

8. The detection system of claim 6 wherein the means for irradiating comprises means for substantially simultaneously irradiating each sample in each capillary with coherent light to cause fluorescence.

9. The detection system of claim 8 wherein the means for substantially simultaneously detecting changes in fluorescent emission comprises a single detector.

10. A multiplexed fluorescence detection system for use with capillary electrophoresis to detect target species in samples comprising:
    (a) an array of at least two capillaries each having an intake end, an outflow end, and an annular wall wherein at least a portion of the wall is translucent to light having a wavelength of about 200–1500 nm, the intake end being in fluid communication with a sample so that the sample is drawn into the capillary;
    (b) means for irradiating each sample in each capillary to cause fluorescence of the target species; and
    (c) a single detector for substantially simultaneously detecting changes in fluorescent emission.

11. The detector system of claim 10 wherein the capillary array comprises at least about 100 capillaries.

12. The detection system of claim 10 wherein each capillary has an inside diameter of about 40–100 microns.

13. The detection system of claim 10 wherein the means for irradiating comprises means for substantially simultaneously irradiating each sample in each capillary with coherent light to cause fluorescence.

14. A multiplexed fluorescence detection system for use with capillary electrophoresis to detect target species in samples comprising:
    (a) an array of at least two capillaries each having an intake end, an outflow end, and an annular wall wherein at least a portion of the wall is translucent to light having a wavelength of about 200–1,500 nm, the intake end being in fluid communication with a sample so that the sample is drawn into the capillary;
    (b) an array of at least two optical fibers, each optical fiber having a first end and a second end, the second end of each optical fiber being coupled to a capillary in the array of capillaries;
    (c) means for generating coherent light of a wavelength suitable to cause fluorescence in the target species present in the capillaries comprising collimating means positioned to distribute the coherent light onto the first ends of the optical fibers in a substantially uniform manner so as to substantially simultaneously irradiate the samples in the capillaries; and
    (d) means for detecting changes in fluorescent emission.

15. A multiplexed fluorescence detection system for use with capillary electrophoresis to detect target species in samples comprising:
    (a) an array of at least two capillaries each having an intake end, an outflow end, and an annular wall wherein at least a portion of the wall is translucent to light having a wavelength of about 200–1,500 nm, the intake end being in fluid communication with a sample so that the sample is drawn into the capillary;

(b) means for irradiating each sample in each capillary to cause fluorescence of the target species; and (c) a charged-coupled device based imaging system for substantially simultaneously detecting changes in fluorescent emission.

* * * * *